United States Patent [19]

Gille et al.

[11] Patent Number: 4,712,567

[45] Date of Patent: Dec. 15, 1987

[54] LIQUID METER ASSEMBLY

[75] Inventors: Henrick K. Gille, Van Nuys; Richard S. Willing, Granada Hills; William G. Bloom, Northridge; Bernard Siegel, Los Angeles; Tsang Cheung, La Canada; Richard Lobodzinski, Sunland; Keith Gilroy, Valencia, all of Calif.

[73] Assignee: American Hospital Supply Corporation, Evanston, Ill.

[21] Appl. No.: 712,953

[22] Filed: Mar. 14, 1985

[51] Int. Cl.⁴ ............................................. A61M 1/00
[52] U.S. Cl. ................................... 128/771; 128/760; 128/767
[58] Field of Search ............... 128/771, 760, 767, 768; 604/317, 318, 322; 73/426, 432 A; 171/1, 15, 244

[56] References Cited

U.S. PATENT DOCUMENTS

| | | | |
|---|---|---|---|
| 4,343,316 | 8/1982 | Jesperson | 128/767 |
| 4,390,073 | 11/1981 | Rosen . | |
| 4,402,373 | 9/1983 | Comeau | 128/771 |
| 4,417,585 | 7/1981 | Frank . | |
| 4,447,939 | 5/1984 | Taylor | 128/760 |
| 4,448,207 | 11/1981 | Parrish . | |
| 4,449,969 | 5/1984 | Schweizer | 128/760 |

OTHER PUBLICATIONS

Chambers et al, Instruments for Sampling and Measuring the Volume Output of Urine from Grazing Female Sheep, Medical and Biological Engineering—Nov. 1976, pp. 665-670.

*Primary Examiner*—Edward M. Coven
*Attorney, Agent, or Firm*—Roger A. Williams; Paul C. Flattery; Robert E. Hartenberger

[57] ABSTRACT

A liquid meter assembly for collecting, metering and monitoring liquid is disclosed. The assembly comprises a container for collecting the liquid, an electrically powered strain gauge suspension device for supporting the container and for determining the weight of the liquid collected in the container and a handle on the container for interconnecting with the strain gauge suspension device. A length of tubing is attached to the container and adapted for interconnecting with the source of the liquid. A tubing support system is included on the strain gauge suspension device for fixedly supporting the tubing to substantially inhibit influence on weight determination due to any movement thereon. A power supply is included in the assembly for supplying power to the strain gauge suspension device.

32 Claims, 9 Drawing Figures

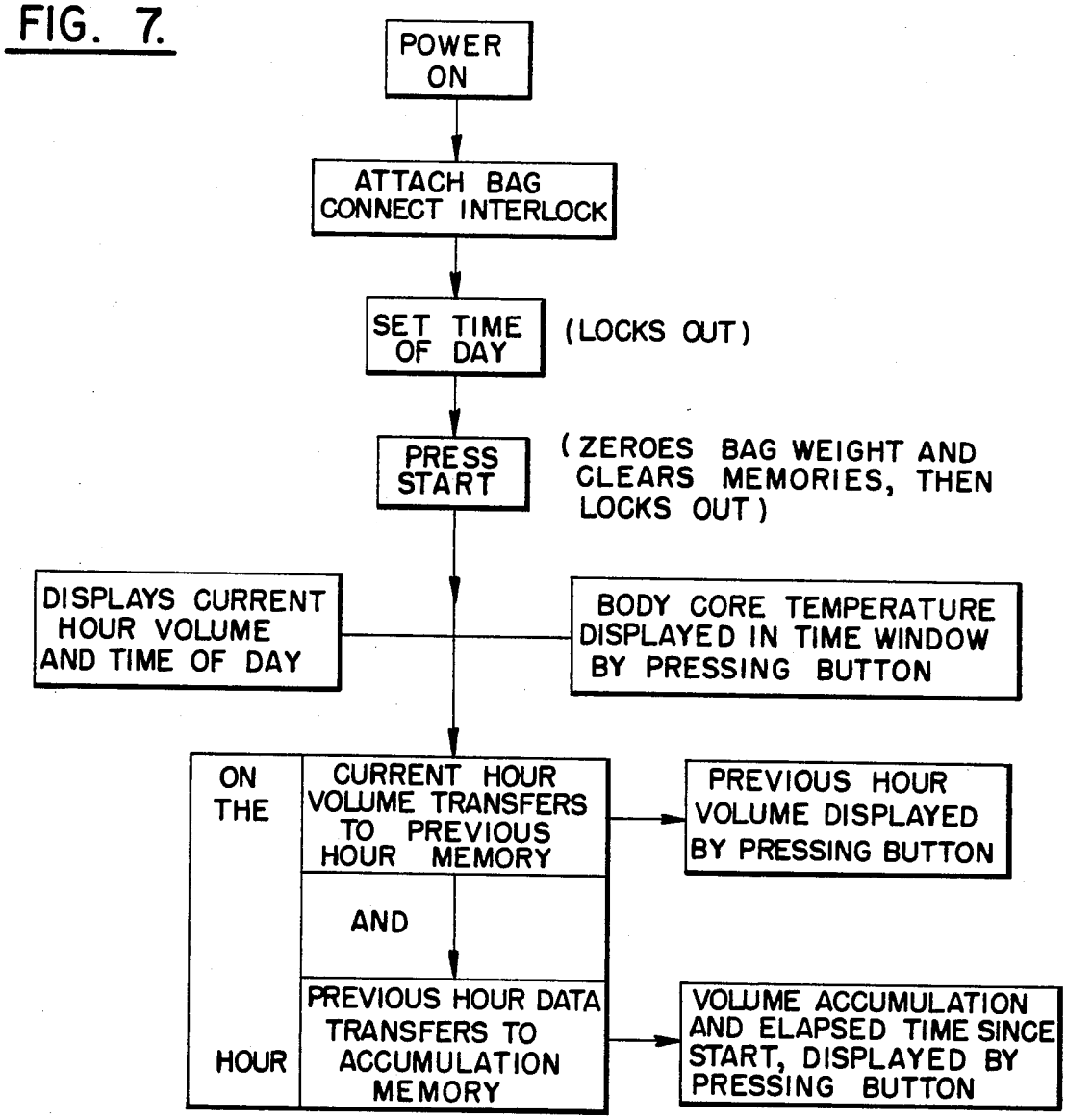
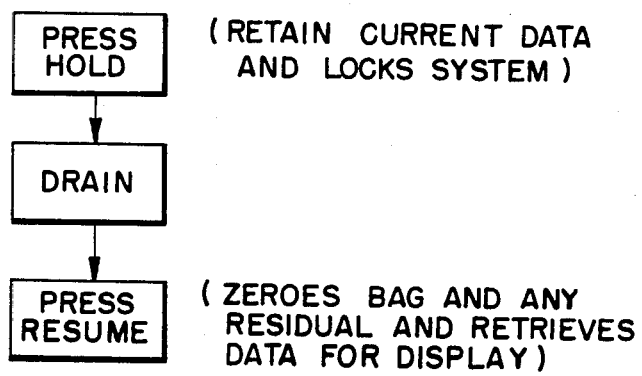

LIQUID METER ASSEMBLY

BACKGROUND OF THE INVENTION

I. Field of the Invention

This invention relates to the field of liquid metering systems and such systems for collecting, metering and monitoring liquids, and more particularly, to an electronically controlled liquid meter or monitor assembly that has particular use in the medical field for collecting, metering and monitoring a body fluid from a living organism, such as urine, which assembly has improved accuracy by including the ability to substantially inhibit any influence on weight determination of the amount of liquid collected due to movement by the living organism.

II. Description of the Prior Art

There are many known devices and systems for the collection and taking of physical measurements or metering of body fluids. In, for example the medical field, in many instances of patient treatment it is often necessary to know at all times the accurate amount of body fluid, such as urine, that is being passed by the patient. It is, in fact, rather conventional in hospitals to collect urine from patients for the measuring and monitoring of urine output as is routinely done for post-operative patients as well as those with urological disorders where, for example, urine output is directly related to renal function. This type of procedure for collecting, measuring and monitoring urine takes on extreme importance because, for example, sudden changes in urine flow, which can occur at any time, can indicate that there is a deteriorating clinical condition in the patient. Changes in urine output have been correlated with changes in cardiac output.

The collection of urine output is typically accomplished by first catheterizing the patient, i.e. a catheter is first passed through the urethra of the patient and the other end of the catheter is connected to a container or drainage bag through a length of flexible tubing. Typically the bag is supported below the patient from the patients bed or other support system, and urine drains by gravity from the patient through the flexible tubing and into the bag.

The prior art describes many different types of systems which are employed to collect and measure urine output. For example, many of the systems use urine collection bags formed of a clear and flexible plastic material which contain indicia in the form of graduations on the bag itself that represents the volume of the urine in the bag. In other systems the urine collection receptacle includes a rigid and clear plastic reservoir in fluid communication with a collection bag which reservoir has volume related indicia and into which the urine initially flows and is stored prior to being emptied into the bag. See, for example, the urine meter bag described in U.S. Pat. No. 4,305,405. Both of these devices present several disadvantages. For example, there is definitely a lack of accuracy in obtaining measurement readings that are made using the printed indicia and there is often a degree of difficulty in reading these devices depending on where they are positioned. Furthermore, the urinary output measurements and monitoring is dependent upon a person coming at precise time intervals to obtain and record the measurements. This is often difficult to do. In addition, the bags with reservoirs require someone to empty the reservoir so that it has room to fill again with urine.

There are many other types of mechanical, electromechanical, and electronic devices used for metering, monitoring and/or collecting body fluids, such as urine. Aside from many of these devices lacking a certain degree of accuracy, they often present problems dealing with safety, high cost to manufacture and/or to operate, lack of portability and general difficulty to use. However, regarding accuracy, many of these systems are often confronted with the inaccurate measurements regarding the amount of urine collected due to the influence of patient movement on the measuring or weighing device used within the system. This is particularly true because the patient is generally connected to the weighing device by flexible tubing. See, for example, the systems described in U.S. Pat. Nos. 4,343,316, 4,390,073, 4,417,585 and 4,448,207 and the article in Medical and Biological Engineering, November, 1976, on pages 665–670 entitled "Instruments for Sampling and Measuring the Volume Output of Urine from Grazing Female Sheep" by Chambers et al.

It is also known in urine output measurement systems to use an ultrasound measurement technique for determining the height of a column of urine in a rigid walled container and deducing from that height the volume of the liquid.

SUMMARY OF THE INVENTION

It is therefore a primary object of the present invention to provide a system for collecting, metering and monitoring of a body fluid, such as urine, substantially devoid of the above-noted disadvantages.

Another object of the present invention is to provide a system for collecting, metering and monitoring of a body fluid that is accurate, and whose accuracy is not interferred with due to movement of the fluid containment system, or particularly in the case of urine collection, by movement of the patient.

Another object of the present invention is to provide a system for collecting, metering and monitoring of a body fluid that exhibits safety in all respects electrically, operationally and with regard to all materials used therein considering the environment in which the device is used.

Another object of the present invention is to provide a system for collecting, metering and monitoring of a body fluid that exhibits a large degree of portability.

Still another object of the present invention is to provide an electronic system for collecting, metering and monitoring of a body fluid that can operate via batteries and exhibit adequate cell life or recharge interval.

Still another object of the present invention is to provide a system for collecting, metering and monitoring of a body fluid that has adequate displays with respect to the type of information presented to the user and with respect to its use in ambient light conditions.

Still another object of the present invention is to provide a system for collecting, metering and monitoring of a body fluid that offers availability of other features such as the display of body core temperature, time or other information.

Still another object of the present invention is to provide a system for collecting, metering and monitoring of a body fluid that presents to the user a minimum number of controls and a general ease of operation.

Still another object of the present invention is to provide a system for collecting, measuring and monitoring of a body fluid that is reasonably insensitive to ambient temperature or pressure.

A further object of the present invention is to provide a system for collecting, measuring and monitoring of a body fluid which is relatively low in cost.

The foregoing and other objects are accomplished, in accordance with the present invention by providing a liquid meter assembly comprising a container for collecting the liquid, an electrically powered strain gauge suspension means for supporting the container and for determining the amount of liquid collected in the container and a handle means on the container for interconnecting with the strain gauge suspension means. Included in the assembly is a length of tubing attached to the container and adapted for interconnecting with the input of the liquid and means to substantially inhibit any influence on the determination of the amount of liquid in the container by the strain gauge suspension means due to movement of or forces on the tubing attached to the container by some outside force such as a patient. A power supply is included in the assembly for supplying power to the strain gauge suspension means.

The system or assembly of the present invention is directed to the collection, measurement, monitoring and display of the results of measurement of the fluid obtained from a living organism, e.g. the urinary output a hospital patient, electronically by utilizing a strain sensing element bonded to a cantilevered beam. A drainage collection bag is coupled mechanically to a load cell. As the bag fills, its weight causes a deflection of the cantilevered beam inducing strain in the sensing element. This strain is a precise and accurate measurement of the weight of the fluid accumulated in the drainage bag. The device measures urine amount with regard to its weight, and using a microprocessor and specific software instructions, converts weight to volume by accounting for urine specific gravity, i.e. performing a mathematical conversion. The software converts strain readings to volume by multiplying average urine specific gravity according to the formula:

$$\text{Volume displayed} = \frac{\text{Weight Measured}}{\text{Specific Gravity}}$$

Such an electronic measurement device is described in copending and commonly assigned application Ser. No. 711,876, filed Mar. 14, 1985, for "Electronic Measuring and Display Apparatus" by Gille et al.

One of the important features of the overall assembly in accordance with the invention is the built-in accuracy which the assembly has in comparison to prior systems due to the fact that the liquid container, the weight of which is being measured, is made independent from external forces on the container primarily in the form of pre-stress or memory and external movement (e.g. movement by a patient connected to the assembly) both of which can be exerted on the flexible inlet tube that is attached to and feeds a liquid from the patient (such as urine) into the container. Such forces are undesirable as they are transferred to the device measuring the amount of liquid in the container, and can thereby cause serious misloadings on the measuring device and subsequent errors in the readings of the amount of liquid in the bag. This type of error which can lead to an incorrect diagnosis of the condition of a patient, is avoided by employing the assembly of this invention.

To substantially eliminate the normally existing pre-stress or memory in the flexible tubing leading to the container prior to using the container in the system, a handle assembly having a detachable arm is used. The specific details of this handle assembly are described in copending and commonly assigned application Ser. No. 711,878, filed Mar. 14, 1985, for "Handle Assembly for a Liquid Containing Bag" by Bloom et al. The detachable arm described therein holds the soft flexible drainage tubing in a fixed position during such procedures as general handling, sterilization, and storage. The flexible tubing, made of a thermoplastic material, relaxes or loses its pre-stress or stress memory over time and temperature to its neutral minimum force position or what can be called its unstressed and relaxed condition. When the detachable arm is broken off the handle at the time of use of the bag, the portion of the flexible tubing leading to the drainage bag will exert little or no force on the measuring device used to weigh the amount of liquid in the bag thereby avoiding any error in the weight measurement, or certainly minimizing the error to an acceptable level (e.g. in urine collection, plus or minus 2 grams at 50 cc urine). The length of flexible tubing which can interfere with weight measurements, i.e. the length of tubing that is annealed to avoid such interference, extends substantially along the same vertical plane as the hanging drainage bag, lying along the handle within a channel located in the detachable arm and into the drainage bag. The channel in the detachable arm serves to support the soft flexible tubing to prevent kinking and also ensures that the position of the tubing is maintained to avoid bending movements which would otherwise occur if the tubing was allowed to hang loosely from the bag and lie offset from the plane of the bag prior to use.

When the assembly is used in accordance with the invention, the length of flexible tubing extending to the liquid holding container is fixed so as to essentially decouple the container, which is supported on a weighing device, from the living organism supplying the liquid, e.g. the patient. Thus, any expected influence that such patient movement has on weight measurements taken on the measuring device is also substantially eliminated.

The assembly in accordance with the invention can include a temperature probe for sensing the temperature of the living organism. The device senses the temperature electrically and outputs a signal representing a value of the temperature which can also be displayed by the microprocessor controlled readout device.

Furthermore, the assembly in accordance with the present invention provides the capability of continuously monitoring fluid output. Data can be transmitted in incremental rate or cumulative amounts. Data can also be transmitted to remote devices including but not limited to computers, recorders, printers, visual displays, alarms or similar devices.

BRIEF DESCRIPTION OF THE DRAWINGS

For a better understanding of the invention as well as other objects and further features thereof, reference is made to the following detailed disclosure of this invention taken in conjunction with the accompanying drawings wherein:

FIG. 7 is a block diagram of the sequence of steps in the operation of the measurement and display device used in the assembly;

FIG. 8 is a block diagram of a further sequence of steps in the operation of the measurement and display device.

DESCRIPTION OF THE PREFERRED EMBODIMENTS

Figure 1:
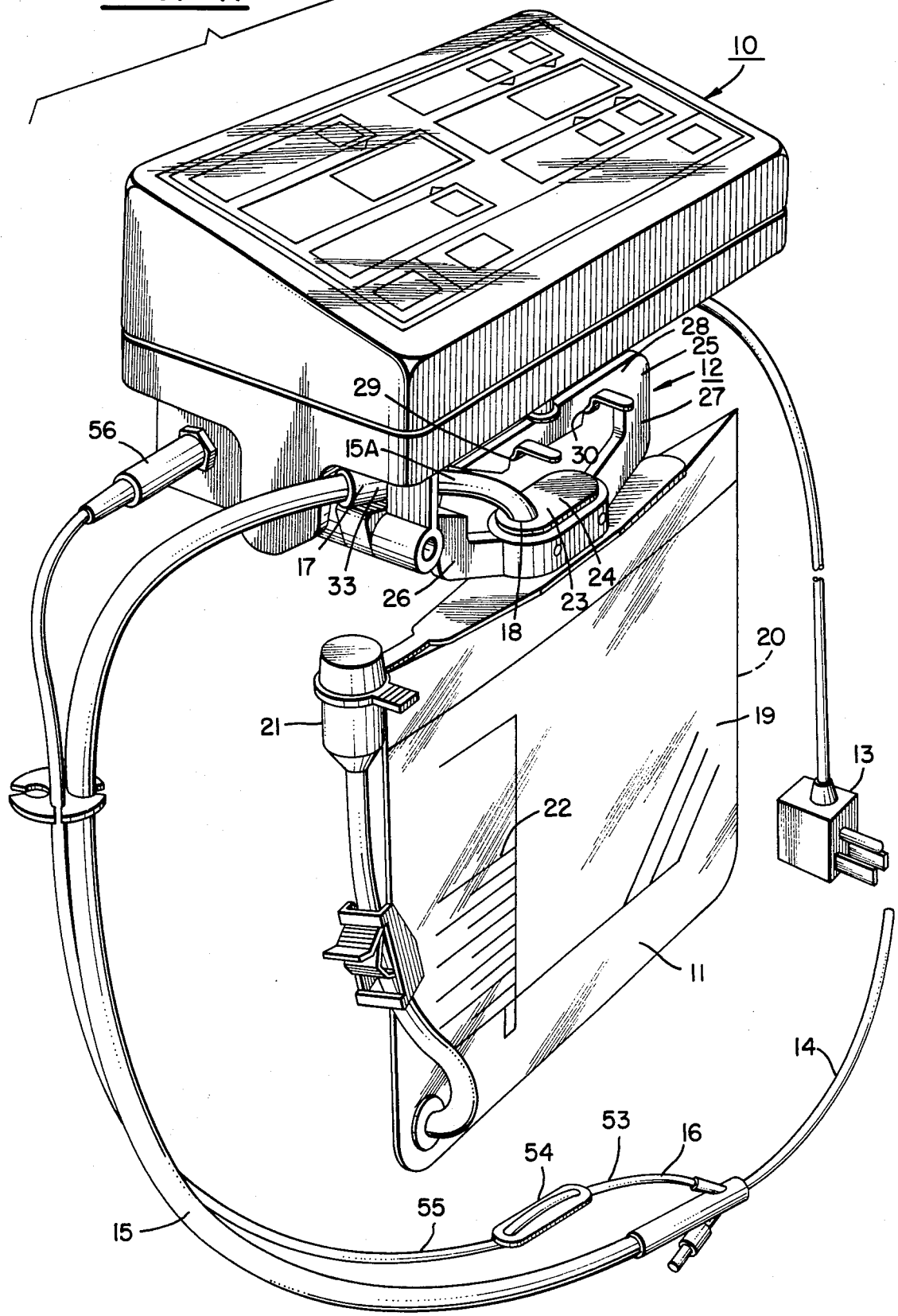
FIG. 1 is a perspective view of a urine meter assembly in accordance with the invention.

The liquid meter or monitor assembly in accordance with the invention used for collecting a body fluid from a living organism, such as urine, electronically measuring the amount of urine collected and displaying the measured results is shown in FIG. 1. The basic components of this assembly include a liquid measurement and display device 10 (the device described in copending and commonly assigned application Ser. No. 711,876, filed Mar. 14, 1985, entitled "Electronic Measuring and Display Apparatus" by Gille et al, a liquid drainage bag 11, a handle assembly 12, a power supply 13 that provides an electrical charge to the batteries used in the measurement and display device, a catheter 14 for obtaining the liquid e.g. urine, from the patient and flexible tubing 15 for assisting in getting the liquid from the catheter to the drainage bag. A core temperature probe 16 for sensing the temperature of the patient and electrically sending a signal of the sensed temperature to device 10, can be included.

THE DRAINAGE BAG AND HANDLE ASSEMBLY

Figure 2:
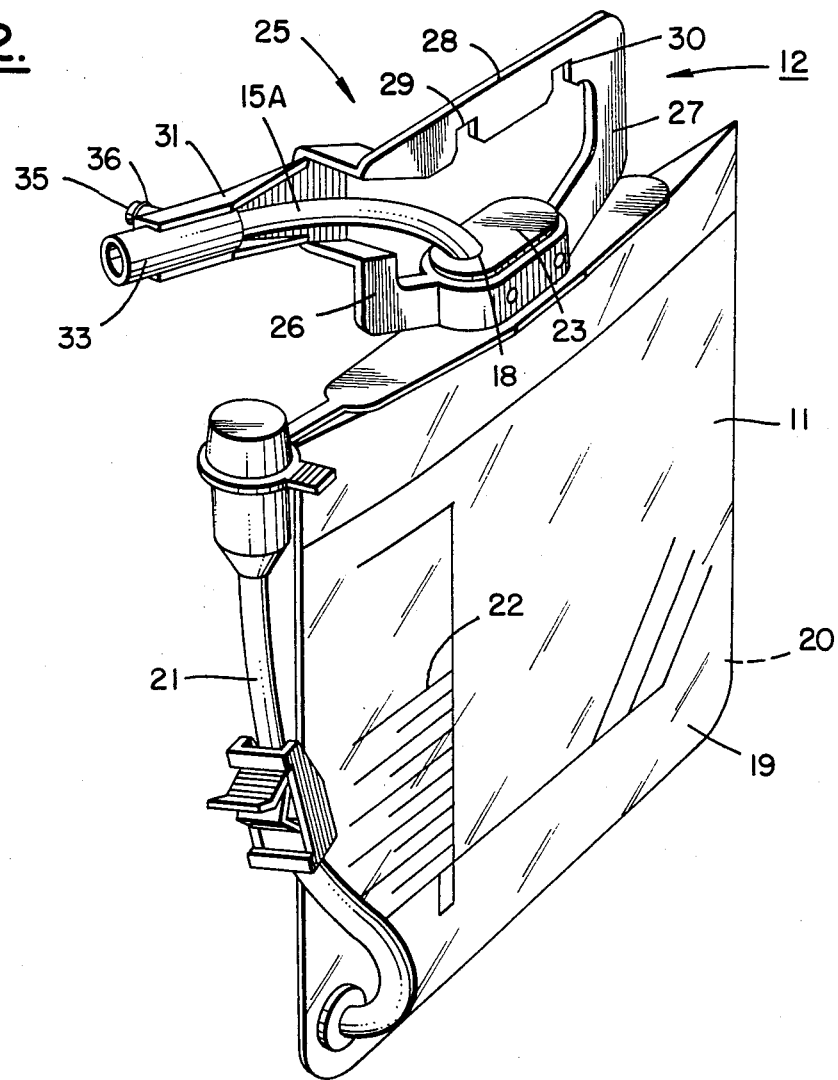
FIG. 2 is a perspective view of a urinary drainage bag including a handle for supporting the bag, the handle including a detachable arm.
Figure 3:
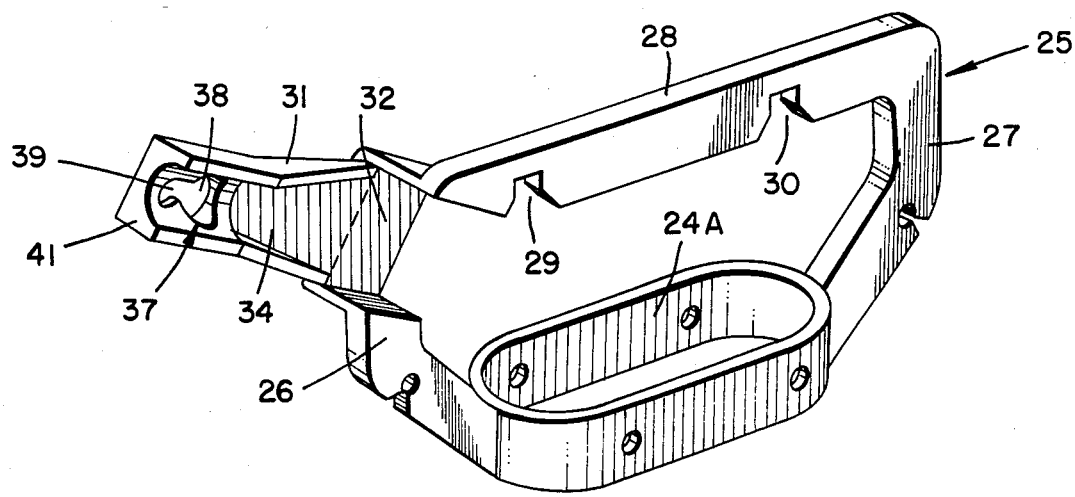
FIG. 3 is a perspective view of the embodiment of a detachable arm as shown in FIG. 2.
Figure 4:
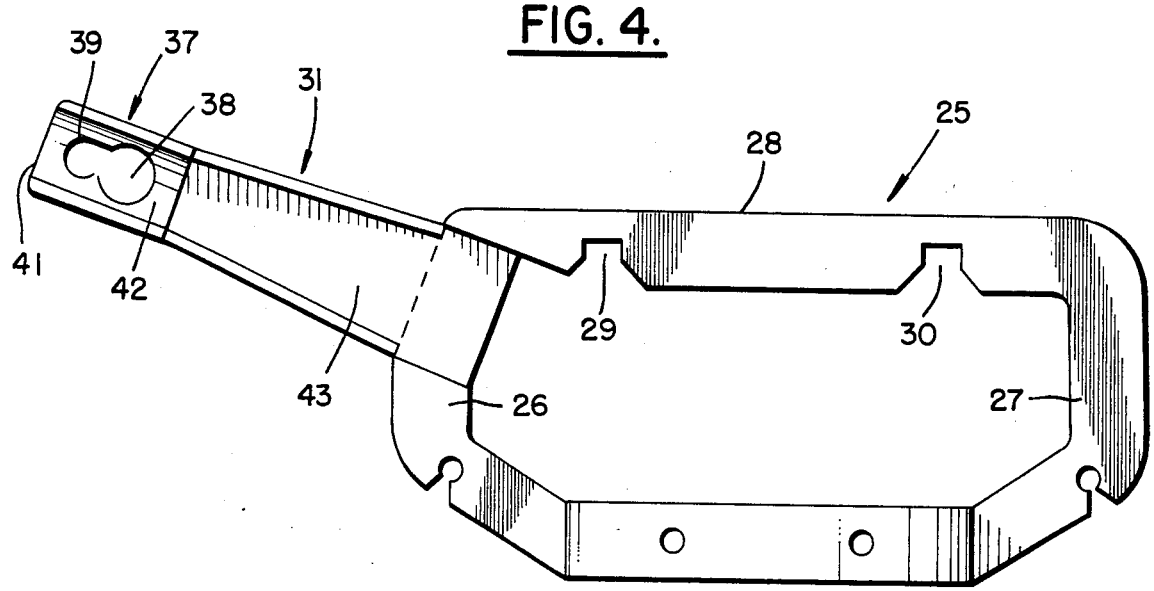
FIG. 4 is a front plan view of the embodiment of a handle assembly for the drainage bag with a detachable arm secured thereto as shown in FIG. 2.

A receptacle for containing a liquid (which for purposes of describing one preferred embodiment of this invention will be described and shown in the form of a urinary drainage bag, e.g. a disposable urinary drainage bag) including a handle assembly therefore and flexible drainage tubing leading to the bag, is shown in FIGS. 2, 3 and 4. The system as defined by the present invention for collecting the urine includes a urinary drainage bag 11, a handle assembly 12 and a critical length of flexible drainage tubing 15A that extends from approximately the point 17 at which the tubing is secured to the handle assembly to the point 18 where the tubing enters the urinary drainage bag. As is common in the art, urinary drainage bag 11 can be provided with a drain 21 which can be clamped off so that the bag can be periodically emptied and can also include an air vent, bacteria filter, drip chamber, antireflux valve, etc. Located on the front portion of the bag can be indicia 29 that indicates the approximate liquid volume of urine in the bag. This is typically included as a backup to the system to enable an operator to directly read the volume of the liquid in the bag if this becomes necessary. The bag is also provided with an inlet opening 23 on the top portion of drip chamber 24 formed of a rigid plastic material. Included in the system is flexible drainage tubing 15 which connects to a catheter that is inserted within the urethral canal of the patient for the purpose of collecting the patients urine. The critical length of flexible tubing 15A can be a portion of or separately interconnected to the flexible drainage tubing 15. In use, an end of the flexible drainage tubing is connected to the distal or funnel end of a catheter. Urine drains through a drainage eye in the end of the catheter, through the catheter and flexible drainage tubing into bag 11.

Bag 11 and all flexible drainage tubing are preferably formed of a thermoplastic material. Any suitable thermoplastic material or materials known in the art may be used that have the desired properties of flexibility, durability, sterlizability and inertness. Generally, effective results are obtained by using a material such as a polyvinylchloride. The flexible drainage tubing is formed of a thermoplastic material which enables the tubing to (i) relax to a preselected contour, thereby relaxing the tubing to lose its prestress condition or stress memory and end up in a neutral, minimum force position and (ii) obtain a desirable shape or contour therein, i.e. a shape imparted to the tubing that will result in the least amount of physical interference when the flexible tubing is put to use in the assembly.

When it is desired to obtain the weight of the liquid within bag 11 it is, of course important to avoid the introduction of any errors in the weight readings. One of the problems with the use of flexible plastic drainage tubing is that it is subject to having a prestress or memory such that when it is secured to the bag, and the bag is placed on a weighing instrument, misloadings can result. To substantially remove this pre-stress or memory within the flexible drainage tubing, particularly length of tubing 15A, and thereby avoid introducing any errors in determining the weight of the urine in the bag, a length of flexible drainage tubing 15 leading to the urinary drainage bag is first supported by handle assembly 12. The critical length of tubing 15A lying between points 17 and 18 is then subject to a thermoforming or annealing process so that a preselected contour is placed into the tubing and the previously existing pre-stress or memory condition is substantially removed. The flexible tubing relaxes over time and temperature to its neutral or minimum force position. The tubing 15A is also thermoformed or annealed to a contour such that it lies substantially in the same vertical plane as the drainage bag when the bag is in a hanging position.

The thermoforming of the tubing is preferably accomplished during a heat treatment or a sterilization process at which time the urinary bag, all the flexible drainage tubing 15 including the critical length of tubing 15A and handle assembly are sterlized, perferably by exposure to ethylene dioxide for several hours at temperatures that are sufficiently high enough to permit the thermoforming to occur without damaging any portions of the system due to overheating. A specific thermosetting process that is preferred, in accordance with this invention, is the procedure described in commonly assigned and copending application Ser. No. 712,572, filed Mar. 14, 1985, entitled "Sterilization Process" by Bloom et al, the content of which is hereby Incorporated by Reference into this application.

As clearly shown in FIGS. 3 and 4, handle 25 includes two leg members 26 and 27 and a connecting member or grasping bar 28 that has two spaced apart slots 29 and 30 extending down from the handle. Slots 29 and 30 enable one to suspend the bag from a weighing device, such as from a load cell, to measure the weight of the liquid contents of the bag. Projecting from leg member 26 is an elongated arm 31 (i) that is used to help support the flexible tubing during a thermoforming treatment such that a desirable preselected contour is obtained in the tubing and any pre-stress or stress memory condition is substantially removed and (ii) that is easily detached from handle 25. The easy detachment or removal of arm 31 from handle 25 is preferably accomplished by providing at the intersection of the arm and handle, an area 32 of material which has a reduced thickness relative to the thickness of the material forming the arm and the handle. Thus, after heat treatment of sterilization, when it is desired to remove arm 31 from handle 25 so that the liquid meter assembly in accordance with the invention described herein can be used, all that is necessary is that one apply a bending movement to the arm and handle along area 32 until rupturing occurs and the arm breaks away from the handle.

As shown in FIGS. 2, 3 and 4 a length of flexible drainage tubing 15A is supported by elongated detachable arm 31 by placing the end of the tubing located within circular collar member 33 within the narrow portion of channel member 34 on elongated arm 31. The tubing is firmly secured to the arm by providing a fastenr that releasably secures the flexible tubing to the arm in a snap-in manner. This snap-in fastener preferably comprises a projection in the form of a rod member 35 extending from circular collar 33 forming a T-shaped collar. The rod member includes a ridge portion 36 extending around the rod member. The rod member is adapted to be inserted within opening 37 in arm 31 and snapped into a force fit with the arm. Opening 37 preferably is key-hole shaped such that rod member 35 can be inserted within the bottom portion 38 of the opening (larger portion of the opening) and snapped up into a force fit with arm 31 by forcing the rod into the smaller top portion 39 of the opening. Ridge portion 36 is positioned on rod member 35 such that it functions to help lock the rod to the arm when the rod is forced into the top portion 39 of the opening.

When the drainage bag is ready to be used, and after the flexible tubing has been thermoformed to remove the above-described pre-stress or memory and a preselected contour has been set into the tubing, the flexible tubing is removed from arm 31 by forcing the rod member out of engagement with the arm. The detachable arm 31 is then bent about 90 degrees or bent back and forth along reduced thickness line 32 until it breaks away from handle 25 and is discarded. The urinary drainage bag 11, flexible drainage tubing 15 and remaining handle assembly 40 is now ready to collect urine and measure the amount of urine collected.

Figure 6:
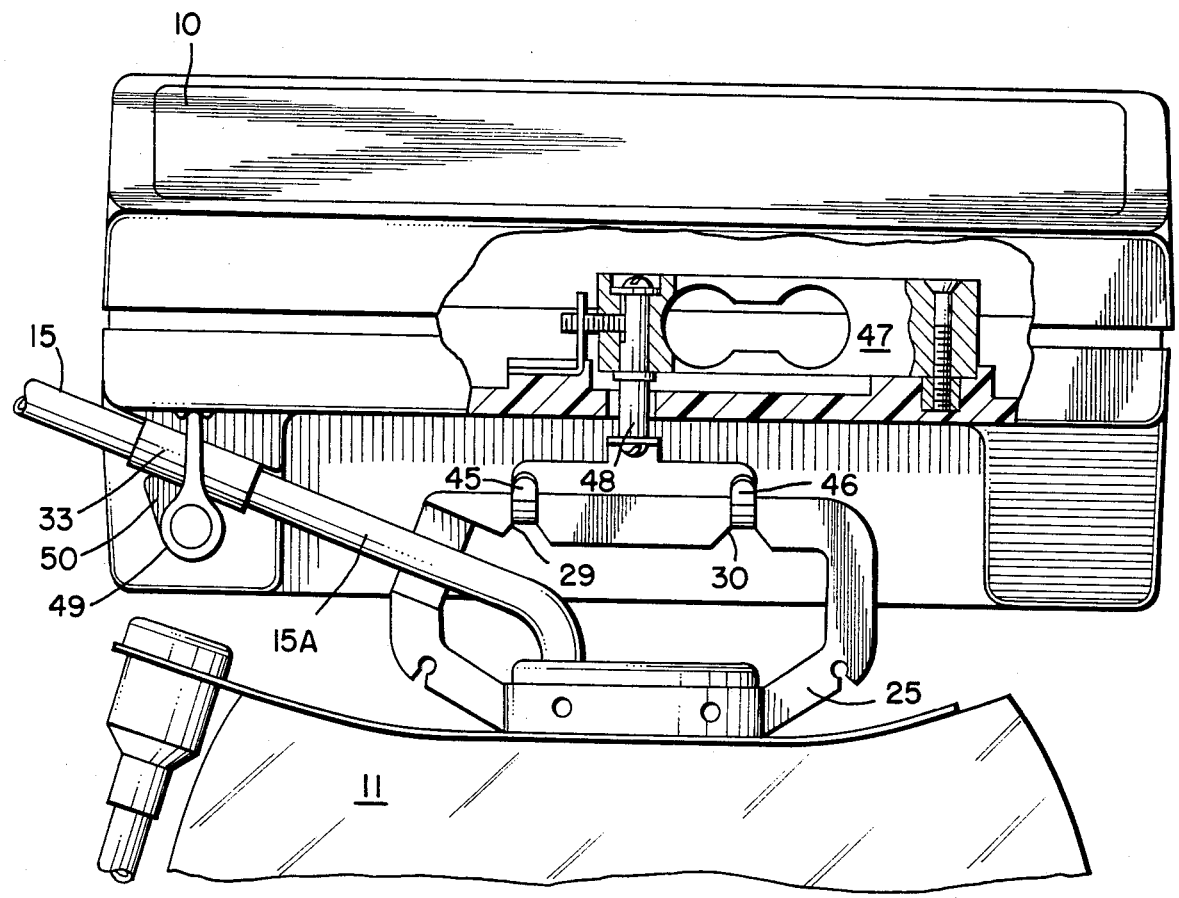
FIG. 6 is a front plan view of part of the components shown in FIG. 5 including a partial break-away portion of the measuring device showing the load cell.
Figure 5:
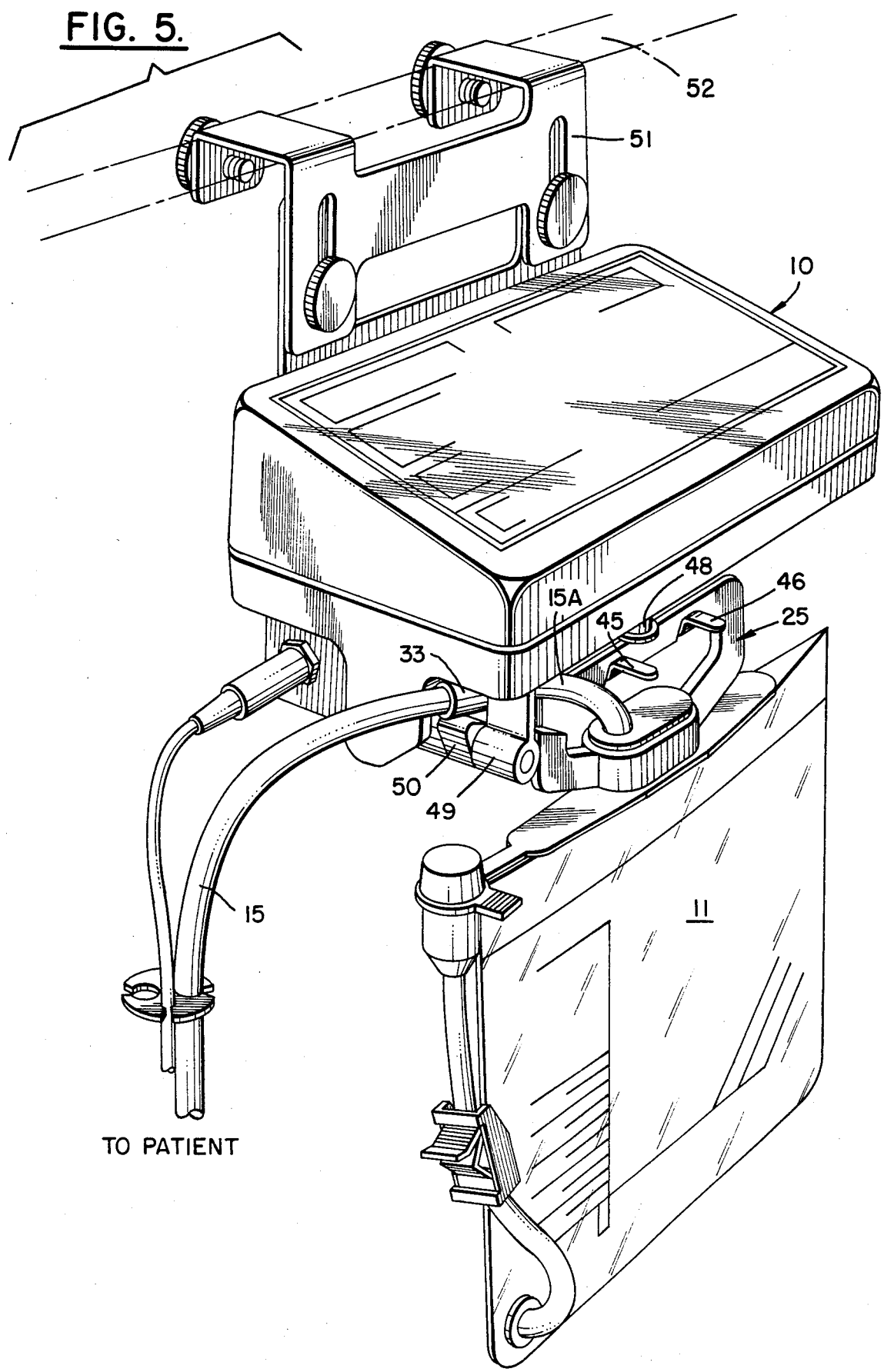
FIG. 5 is a perspective view of a liquid meter assembly including drainage bag, handle assembly and measuring device.

For the measurement of patient urinary output an electronic measuring and display device 10 is employed, as shown in FIGS. 5 and 6, by utilizing a strain sensing element bonded to a cantilevered beam. Urine drainage collection bag 11 is supported by handle 25 via slots 29 and 30 on the two arms 45 and 46 secured to load cell 47 which permit the drainage collection bag to be coupled mechanically by linkage 48 to the load cell in the measurement device. As urine enters the collection bag its weight causes a deflection of the cantilevered beam inducing strain in the sensing element. This strain is a precise and accurate measurement of the amount of fluid delivered to the drainage bag 11, provided however, that the flexible tubing 15–15A is properly mechanically decoupled from the weighing instrument. A major cause of error in taking weight and/or volume measurements of this type is due to extraneous movement and forces, e.g. movement(s) of the patient, to which the flexible tubing is attached, and the resulting influence that such patient movement(s) have on measurements made on the load cell. It was discovered in accordance with this invention that by providing means to fix or support the flexible tubing 15, particularly the length of flexible tubing 15A leading to and attached to the urinary drainage bag 11, one can substantially inhibit any influence on weight determination due to any movement(s) by the patient. It was discovered that bag 11 is essentially decoupled from the patient by fixing or securing the flexible tubing to the housing on measuring device 10. This can be accomplished by providing an opening (not shown) on the housing of device 10 and by releasably fastening the flexible tubing to the housing by inserting rod member 35 within the opening on the housing. Since rod member 35 extends from collar 33 which holds the flexible tubing, the tubing can be fixed or supported by the device thereby decoupling the bag 11 to which the tubing is attached from the patient. The flexible tubing (and in effect the bag) is fixed at three support points. The three fixed or support points are the two arms 45 and 46 extending from the load cell to which the bag 11 is supported via handle 26, and the one fixed or support point where the flexible tubing is fastened or attached to the housing of device 10. In accordance with the present invention, the length of flexible tubing 15A is firmly fixed to device 10 through an interlock connector on the weighing device body. The interlock connector preferably includes a rotatable knob 49 and associated cam 50 which hold the tubing 15A at collar 33 in a snug fit. In practice the tubing 15A is preferably firmly locked to the meter or monitor device 10 by inserting rod 35 on collar 33 into the opening (not shown) on device 10 and turning knob 49 and concomitantly cam 50 to secure collar 33 and corresponding rod 35 into the provided opening. By turning knob 49, cam 50 is caused to pinch against collar 33 and thereby firmly fix and lock the tubing in place. The specific locking mechanism described herein is given by way of an example of one embodiment of the type of locking mechanism that can be used with the present invention to firmly lock the flexible tubing to the device. This locking feature provides an additional backup to decoupling the overall system from movements of the patient.

For supporting the entire assembly to, for example, the patients bed or other support structure, device 10 is secured to mounting bracket 51 which is attached to the bed or other support structure 52.

MEASURING AND DISPLAY DEVICE

With reference now to FIG. 7 there is shown in block diagram form a sequence of the operations of the computer (microprocessor) controlled measurement and display device 10 for providing electrical measurements of the amount of urine collected and the temperature of the person providing the urine sample. This information is displayed on the operator panel of the device as explained in detail in the copending and commonly assigned application referred to above as Ser. No.

711,876. As set forth in FIG. 7, personnel that are operating device 10 initially turn on the power, this being accomplished by use of one of the push buttons on the operator panel. Thereupon a urine collection bag is attached. Then the time of day is set on the device display by the use of push buttons. Then the start button is pressed. Thereafter, various pieces of information appear on the displays, e.g. volume, temperature, etc. It should be noted that when the measuring device is turned on, operating time set and the start button depressed, a weighing is made of the empty bag. This amount is stored in the device memory as the tare for the system. Weight measurements are made by substracting the tare from subsequent readings, and no zero adjustment is required.

In FIG. 8 the drain procedure is disclosed. First the operator presses the button which locks in the data for storage, this data having been obtained during the previous filling of the bag. Thereafter, the bag is drained. Further data can then be taken by pressing the "resume" button.

Figure 9:
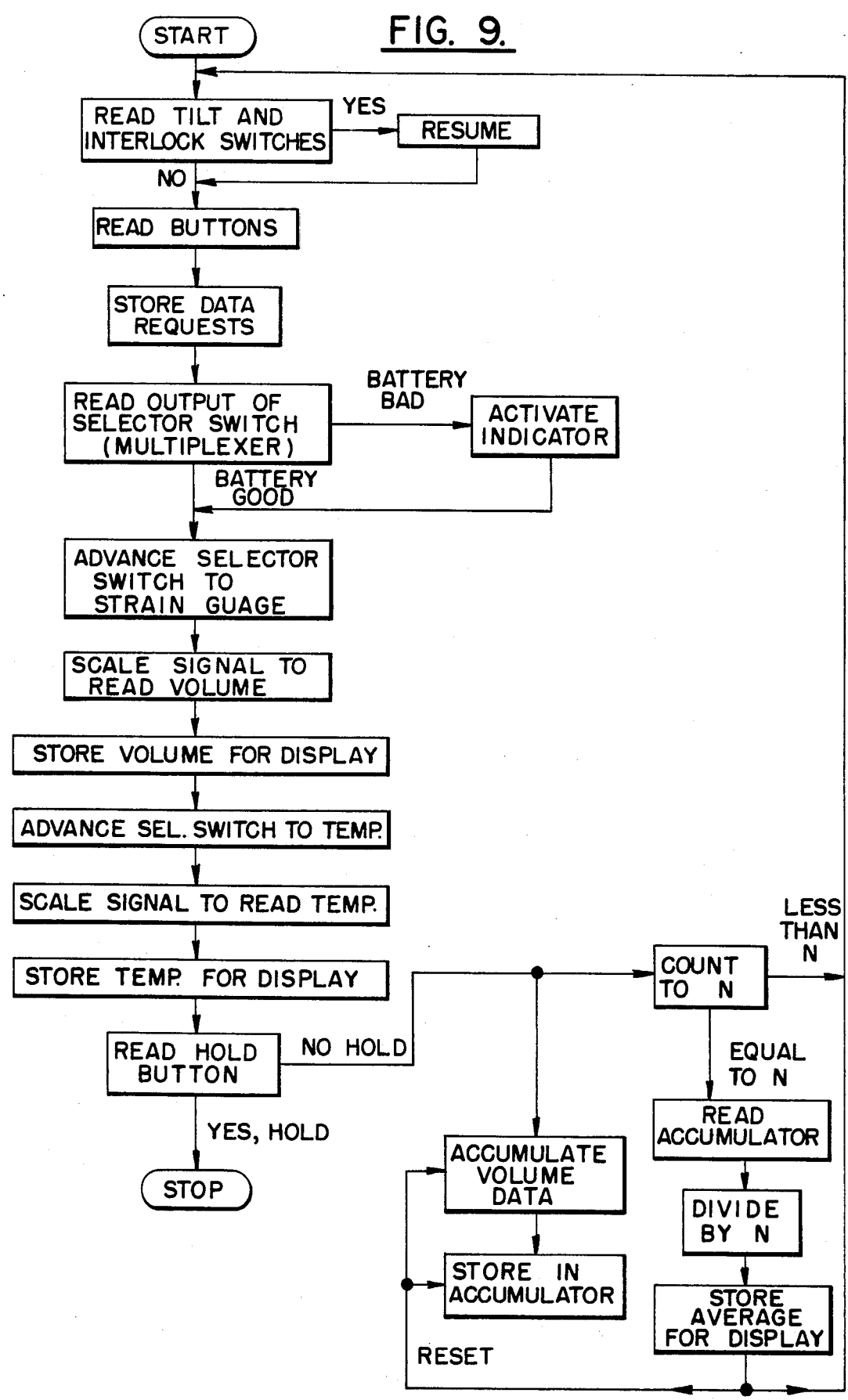
FIG. 9 is a flow chart describing the operation of a computer in the measurement and display device.

With reference also to FIG. 9, there is provided explanation of the operation of the computer portion within the measurement device. The flow chart of FIG. 9 begins with depressing of the start button by operating personnel. Thereupon, the computer reads the signals from a tilt switch and from an interlock switch to determine whether a tilt or interlock condition exits. In the device a tilt switch provides a switch closure when the measuring device is tilted at any azimuthal direction away from the vertical by a preset angle. In the present embodiment, this angle may be advantageously set at 10 degrees. Such switch closure indicates that the output display of liquid volume, on the devices display, will experience an error due to excessive tilt. Also provided is an interlock switch which withholds a required switch closure when the urine tubing is not fully connected indicating that the equipment is ready to operate. If there is excessive tilt or the tubing is not properly connected, the computer signals such problems and waits for a correction of the problem by the operating personnel. Upon correction and a command to resume, the computer then proceeds to read the command of other ones of the busses on the operator panels. These buttons provide for requested data such as temperature or time as well as whether the present reading or a previous reading of urine quantity is to be displayed. The commands for data are then stored.

Thereupon, the computer reads the output of the selector switch, or its multiplexer. The selector switch, in this example of the operation, is to begin in the battery test position. Accordingly, the computer reads the output battery voltage and activates an indicator if the battery is bad due to improper voltage. The computer indicates the status of the battery and then proceeds to advance the selector switch to the position of the strain gauge. The computer then reads the output from the strain gauge and scales the signal to read in volume for display of data. Thereupon, the volume of urine is stored for future display.

The operation of the computer then continues by an advancement of the selector switch to the position for receiving temperature data. The computer reads the temperature data, this being presented as a voltage in digital format, and then scales the signal to read in temperature. The temperature value is then stored for future display. It should be noted that there are many instances where a temperature monitoring catheter as described herein will not be used.

Thereafter, the computer reads the position of the "hold" button to determine if the operator wishes to stop the process, for example, for purposes of draining the bag. Since the operator has not commanded a hold, the computer recycles to the beginning of the program to proceed with a reading of the tilt and interlock switches. If the operator has designated a hold on the operation, then the computer stops.

The foregoing operation, as set forth in FIG. 9 pertains to the major functions of the computer. It is understood that the program can include further loops, such as an averaging of a succession of stored values of temperature or volume for subsequent display of an average value. The foregoing operational procedure provides the operating personnel with the desired information in a convenient and safe fashion.

As an example of such averaging, FIG. 9 further shows a counting operation in the line which extends from the hold button back to the beginning of the program. The counter counts to N where N is the number of data samples, such as 12 samples which are to be averaged together. With each "no hold" condition the computer reads the stored value of the volume of acquired liquid and sums this value with the previously stored value of the amount of liquid. This is an accumulating process. The computer continues to accumulate successive values of the stored liquid. When the desired number of N values have been accumulated, the computer reads the accumulated value, divides this value of N to obtain the average value of the stored liquid and then stores the average value for display. Thereupon, the computer resets the accumulator storage at zero and returns to the beginning of the program. A similar accumulation and averaging loop can also be provided for the averaging of values of temperature.

TEMPERATURE PROBE

The system also includes a temperature sensor means for sensing the core temperature of the patient. This sensor means is preferably a temperature probe that is positioned within the catheter which is then inserted within the urethra of the patient. Thus, the temperature probe can be inserted within the patient for taking precise measurements of temperature which can be directed to the measurement and display device. In use (as shown in FIG. 1) a male connector extending through an arm 53 of the catheter is inserted into a female connector to form connector 54 attached to extension cable 55. Located at the opposite end of the extension cable is an electrical probe 56 that is inserted within the part on the measuring device 10 labeled "TEMP PROBE".

The system described in accordance with the present invention can be used to collect numerous types of liquids including various types of body fluids. One example of such a body fluid is urine, which has been used as a specific example to describe a detailed embodiment of the present invention.

While this invention has been described in conjunction with specific embodiments thereof, it is evident that many alternatives, modifications and variations will be apparent to those skilled in the art. Accordingly, the present invention is intended to embrace all such alternatives, modifications and variations as fall within the spirit and scope of the appended claims.

We claim:

1. A liquid meter assembly comprising:

a container for collecting the liquid;

an electrical strain gauge suspension means for supporting the container and for determining the weight of liquid collected in the container;

a handle means on the container for interconnecting with the strain gauge suspension means;

a length of tubing attached to the container and adapted for interconnecting with the source of the liquid;

means to substantially inhibit influence on weight determination due to any movement of said tubing; and a power supply means for providing power to the strain guage suspension means.

2. A liquid meter assembly according to claim 1 wherein said inhibiting means includes a tubing support on said strain gauge suspension means for fixedly supporting said tubing to said strain gauge suspension means.

3. A liquid meter assembly according to claim 2 wherein said tubing support includes means to releasably fasten said tubing to said suspension means.

4. A liquid meter assembly according to claim 3 further comprising means to lock said tubing to said suspension means.

5. A liquid meter assembly according to claim 1 wherein said liquid is from a living organism.

6. A urine meter assembly for collecting, metering and monitoring urine from a catheterized patient comprising:
   a urinary drainage container for collecting the urine
   a meter device including
   (i) an electrical strain gauge suspension means for supporting the urinary drainage container and measuring the weight of the urine therein and
   (ii) control means for converting the weight measurement to volume; a handle means on the urinary drainage container for interconnecting with the strain gauge suspension means;
   a length of tubing attached to the urinary drainage container and adapted for interconnecting with a urinary drainage catheter inserted into a patient;
   a tubing support means on the meter device for fixedly supporting the tubing to substantially inhibit any influence on weight determination due to any movement of the patient; and
   a power supply means for providing power to the meter device.

7. A urine meter assembly according to claim 6 further including a temperature sensor means for sensing the core temperature of said patient.

8. A urine meter assembly according to claim 7 wherein said temperature sensor means includes a temperature probe within said catheter, the probe being electrically coupled to said meter device.

9. A urine meter assembly according to claim 6 wherein said tubing support means includes three support points.

10. A urine meter assembly according to claim 6 wherein said tubing support means includes one support point located on said meter device wherein said tubing is releasably fastened to said device.

11. A urine meter assembly according to claim 10 wherein said support point on said meter device comprises an opening on said device and said tubing includes a projection thereon adapted to be inserted within the opening.

12. A urine meter assembly according to claim 10 wherein said tubing is fixed to said device through a connector on the meter device which firmly locks said tubing to said device.

13. A urine meter assembly according to claim 12 wherein said connector includes a rotatable knob and associated cam rotatably attached to the meter device.

14. A urine meter assembly according to claim 6 wherein said strain gauge suspension means includes two extending arm members.

15. A urine meter assembly according to claim 14 wherein said tubing support means includes said arm members and a support point on said meter device.

16. A urine meter assembly according to claim 15 wherein said support point on said meter device comprises an opening on said device and said tubing including a projection thereon is adapted to be inserted within the opening.

17. A urine meter assembly according to claim 14 wherein said handle means is freely supported on said arm members.

18. A urine meter assembly according to claim 6 wherein said tubing is formed of a material treated to avoid exerting substantially any influence on weight readings when said container is suported by said strain gauge suspension means.

19. A urine meter assembly according to claim 6 wherein said meter device includes indication means for displaying total urine output, the previous hours urine output or the current hour's urine output.

20. A urine meter assembly according to claim 19 wherein said urine output is displayed in terms of volume measurement.

21. A urine meter assembly according to claim 6 wherein said meter device includes indicator means for displaying lapsed time and body core temperature.

22. A urine meter assembly according to claim 6 wherein said power supply means is battery operated.

23. A urine meter assembly for collecting, metering and monitoring urine from a catheterized patient comprising;
   a urinary drainage container for collecting urine from said catheterized patient;
   a meter device including a housing and an electrical strain guage suspension means for supporting the urinary drainage container and for determining the weight of urine collected in the urinary drainage container;
   a handle means on the urinary drainage container for interconnecting with the strain gauge suspension means;
   a length of tubing attached to the urinary drainage container and adapted for interconnecting with a urinary drainage catheter inserted into the patient;
   a tubing support means on the meter device housing and on the strain gauge suspension means, for fixedly supporting the tubing to substantially inhibit influence on weight determination due to any movement by the patient; and
   a power supply means for providing power to the meter device.

24. A urine meter assembly according to claim 23 further including a temperature sensor means within said catheter for sensing the core temperature of said patient, the sensor means being electrically coupled to said meter device.

25. A urine meter assembly according to claim 23 wherein said tubing support means comprises three support points.

26. A urine meter assembly according to claim 23 wherein said tubing support means includes locking means to firmly lock said tubing to said meter device.

27. A urine meter assembly according to claim 26 wherein said tubing includes a projection thereon adapted to be inserted within an opening in said housing and said locking means firmly locks the projection within said housing.

28. A urine meter assembly according to claim 27 wherein said locking means comprises a rotatable knob and associated cam rotatably attached to the meter device.

29. A urine meter assembly comprising:
- a urinary drainage container for collecting urine from a catherized patient;
- an electrical strain gauge suspension means for supporting the urinary drainage container and for determining the weight of urine collected in the urinary drainage container;
- a handle means on the urinary drainage container for interconnecting with the strain gauge suspension means;
- a length of tubing attached to the urinary drainage container and adapted for interconnecting with a urinary drainage catheter inserted into the patient;
- means to substantially inhibit any influence on weight measurements due to any movement of the catheter or patient; and
- a power supply for providing power to the strain gauge suspension means.

30. A urine meter assembly according to claim 29 wherein said inhibiting means comprises at least one point on said strain gauge suspension means at which said tubing is affixed.

31. A urine meter assembly according to claim 29 wherein said inhibiting means comprise three fixation means on the urine meter assembly for affixing the tubing at three points along the tubing to the urine meter assembly.

32. A urine meter assembly according to claim 29 wherein said tubing is fixed to said device by a means which firmly locks said tubing to said device.

* * * * *